United States Patent [19]

Boehringer

[11] 4,026,284
[45] May 31, 1977

[54] PRESSURE RELIEF VALVE FOR ANESTHETIC ADMINISTRATION

[76] Inventor: John R. Boehringer, 427 Parkview Drive, Wynnewood, Pa. 19096

[22] Filed: Aug. 29, 1975

[21] Appl. No.: 609,072

[52] U.S. Cl. .............................. 128/188; 128/276; 137/614.2

[51] Int. Cl.² ........................................ A61M 16/00

[58] Field of Search ........ 251/122; 128/188, 145.8, 128/142, 142.4, 274, 2.08, 276, 277, 278, 297, 298; 137/533.11, 614.2, 801

[56] References Cited

UNITED STATES PATENTS

| 717,437 | 12/1902 | McCall | 251/122 |
|---|---|---|---|
| 1,919,232 | 7/1933 | Lee | 251/122 |
| 2,941,542 | 6/1960 | Jacobson | 137/533.11 |
| 3,084,691 | 4/1963 | Stoner | 128/278 |
| 3,360,807 | 12/1967 | Haidek et al. | 128/276 |
| 3,575,196 | 4/1971 | Marrese | 137/614.2 |
| 3,761,053 | 9/1973 | Bedo et al. | 251/122 |
| 3,908,987 | 9/1975 | Boehringer | 272/99 |

Primary Examiner—Robert W. Michell
Assistant Examiner—Henry J. Recla
Attorney, Agent, or Firm—Paul & Paul

[57] ABSTRACT

A "pop-off" valve which is inserted in the patient anesthesia circle controllably relieves pressure build up into a vacuum exhaust system. A vertically disposed housing has a lower chamber accessing the circle, and an interconnected upper chamber connected to the vacuum exhaust. In the lower chamber a nylon ball in a frustoconical cavity provides predetermined back pressure whether opened or seated. A characterized plug in screw engagement with the housing mates with a formed opening between the two cavities, and provides facility to close the valve or to occlude flow by a predetermined amount.

6 Claims, 3 Drawing Figures

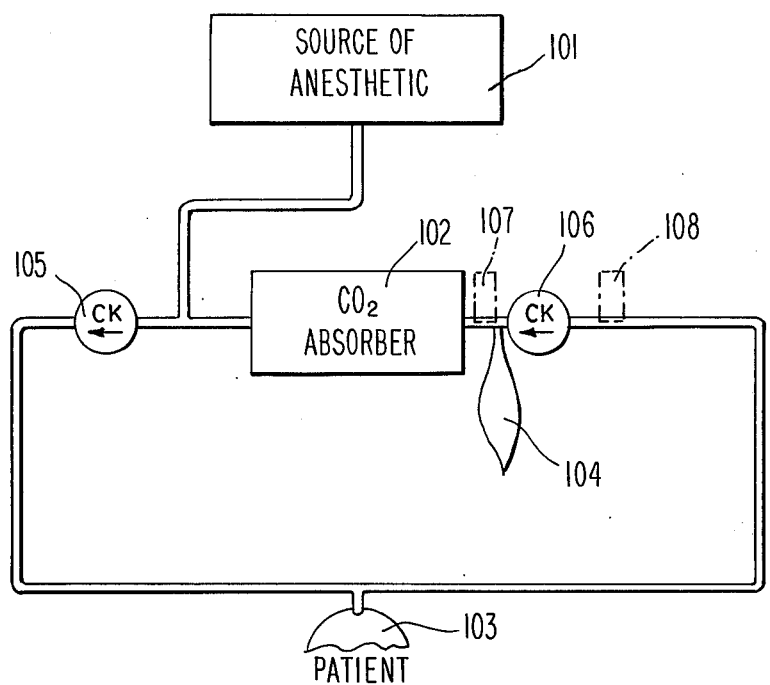
Fig. 1
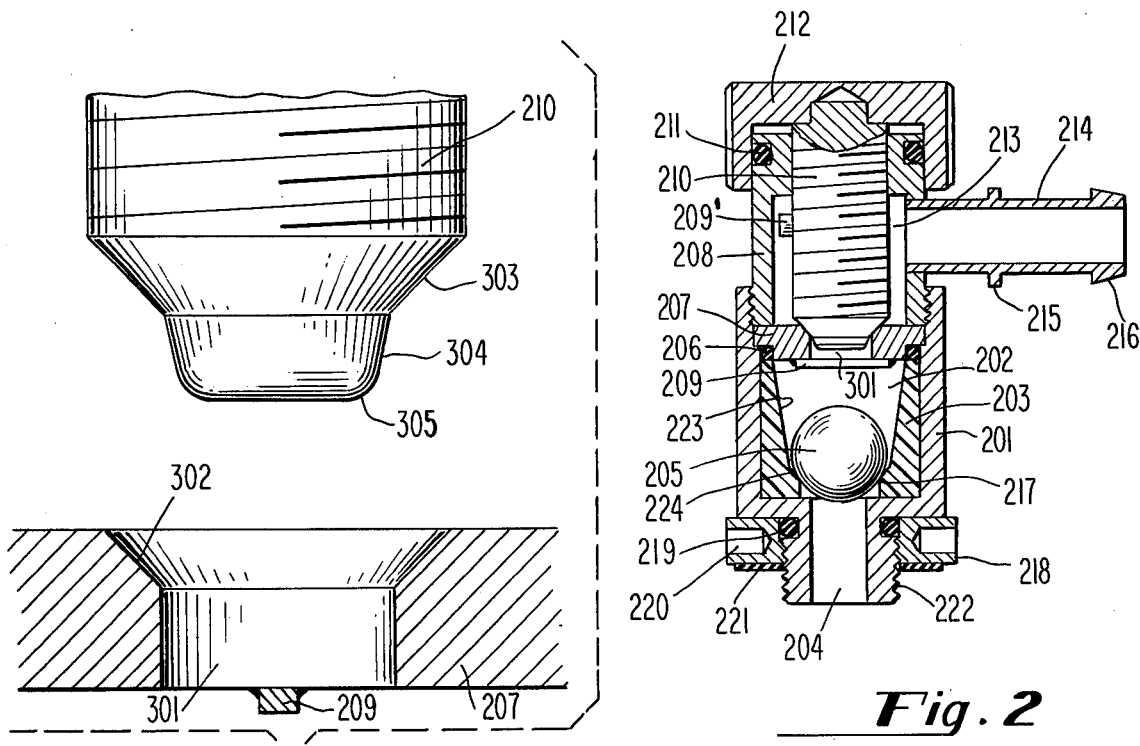
Fig. 2
Fig. 3

PRESSURE RELIEF VALVE FOR ANESTHETIC ADMINISTRATION

BACKGROUND OF THE INVENTION

This invention relates to apparatus for the administration of anesthesia, and more particularly to apparatus for preventing unwanted pressure build up in the patient anesthesia circle.

A conventional method for administration of gaseous anesthesia features the so-called patient anesthesia circle, wherein oxygen and the anesthetic gases are coupled to the patient for inhalation, and exhaled gases are passed through a carbon dioxide absorber and back to the entry point of oxygen and anesthesia. One way valves isolate the patient from the source of anesthesia and the carbon dioxide absorber, and a reservoir bag is provided on the patient side of the valves. In such a system, it is important to provide apparatus in the circle to prevent pressure build-ups which may be harmful or fatal to the patient. To this end, pressure relief valves conventionally are included, which are designed to open the system to the atmosphere when pressure exceeds a predetermined threshold. The most common designs of such valves feature diaphragms or pistons which are held in place by the force of a spring. When pressure in the circle is sufficient to deflect the spring, the diaphragms or pistons are displaced, and pressure is relieved.

More recently, attention has been given to the fact that such pressure relief expells anesthesia gases into the atmosphere, and undesirably exposes operating room personnel thereto. Hence, vacuum exhausts have been developed whereby gases which are expelled from the anesthetic circle during excess pressure times are conveyed safely out of the operating room. Vacuum exhaust systems have complicated and accentuated difficulties which sometimes occurred in the operation of conventional pressure relief valves. In some cases, the diaphragms stick closed, allowing for the dangerous condition of hyperinflation of the patient. Also, the vacuum pressures often cause diaphragms or pistons to vibrate badly. Such vibration not only is annoying to the staff and accelerates wear of the valve, but more dangerously may impress oscillation on the system pressure, which also may be quite detrimental to the patient.

It is accordingly a primary object of the present invention to provide pressure relief apparatus for the patient anesthesia circle which functions synergistically with the vacuum exhaust, which avoids the problems of vibration and oscillation, and which will not stick in use.

SUMMARY OF THE INVENTION

The present invention involves a "pop-off" valve utilizing a combination of a positive end pressure ball in a suitably formed chamber, interfacing with the vacuum exhaust through an accurately controllable characterized plug and opening combination. The ball and chamber arrangement allows for a carefully controlled back pressure which neither vibrates nor allows for the possibility of sticking in place. The adjustable plug allows for positive shut off, positive opening, and a carefully controllable flow which suits the anesthesiologist clinically.

In an illustrative embodiment, a vertically disposed housing forms a frustoconical cavity, the lower end of which interfaces the patient anesthetic circle. Within the cavity is a ball of predetermined specific gravity seated in the upwardly broadening chamber. At the outlet of the cavity is a seat having a shaped orifice, into which a valve plug fits. The plug is in threaded engagement with the housing, and is shaped in accordance with the flow variation desired for the anesthesiologist.

DESCRIPTION OF THE DRAWINGS

FIG. 1 shows in symbolic form a conventional anesthetic administration set-up;

FIG. 2 shows in cross section an illustrative embodiment of the present invention; and FIG. 3 shows a detailed representation of a portion thereof.

DETAILED DESCRIPTION

Referring first to FIG. 1, there is shown in symbolic form a conventional anesthesia adminstration set-up. The elements shown in discrete fashion in FIG. 1 may actually by independent or may constitute an integral machine system, and it is to be understood that their presentation here is solely for the purpose of illustration, and for the proper environmental setting of the present invention. The setup shown in FIG. 1, which is commonly referred to as the "patient anesthesia circle", or the "patient circle", constitutes apparatus for administering anesthetic gases premixed in appropriate proportions with oxygen, for absorbing carbon dioxide from gases exhaled by the patient, and for maintaining proper pressures and administration rates while in use. A source of anesthetic 101 typically includes sources of oxygen, and of anesthetic gases such as nitrous oxide or the like. Those gases, appropriately proportioned and mixed by the anesthesiologist, are coupled through a one way or "check valve" 105, and thence to the patient 103, where they are administered through a mask, a trachea tube, or the like. Exhaled gases from the patient 103 are blocked from flow in the reverse direction by the valve 105, and therefore are coupled through a check valve 106 to a carbon dioxide absorber 102. The absorber 102 then couples the filtered gases back toward the valve 105, where they are safely intermixed with gases from the source of anesthetic 101. It is also conventional to provide a storage reservoir bag 104 in the exhalation branch of the patient circle. The reservoir bag 104 serves to capture peak exhaust surges, and permits the anesthesiologist to pump pressure against the patient 103 if clinically desired.

In the prior art, the desirability of providing pressure relief valves, also sometimes known as "pop-off" valves, has been accomplished by insertion of valve apparatus at positions indicated in phantom at 107 or 108 of the circle of FIG. 1. Such positions also are suitable for positioning of a pressure relief valve in accordance with the principles of the present invention, but it to be understood that the positioning of the apparatus set forth hereinafter is freely variable in accordance with the clinical needs of the anesthesiologist and other design constraints imposed upon those or ordinary skill.

FIG. 2 shows a cutaway view of a preferred embodiment of the present invention. In FIG. 2, several discrete parts are interconnected by insertion, interference fit, and/or threaded engagement in order to form the entire apparatus, but it is to be understood that many such aspects are dictated only by the state of the fabrication arts including high precision molding and machining.

Hence, housing elements 201 and 208 are in threaded engagment to provide a housing means having an inlet port 204 and an outlet port 301. Advantageously, the valve of FIG. 2 is vertically disposed with the inlet port 204 accessing the patient circle, such as at positions 107 or 108 of FIG. 1, and with an exhaust nozzle 214 being coupled to a vacuum exhaust system. The lower portion of the housing 201 is provided with a threaded portion 222 and a sealing gasket 221 for sealable mounting of the valve of FIG. 2 to a corresponding female element in the patient circle. Further, the nozzle 214 is provided with circumferentially disposed flanges 215 and 216 for an interference fit with a flexible hose from the vacuum exhaust system.

The housing 201 forms a frustoconial cavity 202 therein, which preferably is accomplished by insertion of a machined plastic insert 203 into the outer housing 201, although it is to be understood that the portions 201 and 203 may be integral in accordance with the state of the molding and machining art. Within the cavity 202 is a ball 205 which normally seats in the lower portion of the cavity 202, and which is raised up into the cavity by sufficient pressure from gases at the input port 204. The top portion 207 of the cavity 202 defines an outlet port 301 for the cavity 202 which when unblocked leads through a chamber 213 to the exhaust nozzle 214. In order to prevent occlusion of the outlet port 301 by the ball, 205, a transverse bar member 209 is provided beneath the port 301. For purposes of fabrication, the top portion 207 is conveniently embodied as a washer like element which fits in sealable registry with the housing 201 over an O-ring seal such as 206. Such seal is promoted by tightening of the upper portion 208 of the housing downwardly against the lower portion 201.

As may be seen more clearly in FIG. 3, the outlet port 301 of the frustoconical cavity 202 is formed to cooperate with a plug 210, which in turn is in threaded engagement with the upper part 208 of the housing, and which is adjustably controlled by manipulation of a control knob 212. More particularly, the portion of the plug 210 which engages the top 207 of the cavity 202 is known as a "characterized" configuration, in that it is machined to have varying configurations 303, 304, and 305 at its lower end, thereby providing predetermined variable flow occlusion depending which part of the plug 210 engages the opening 301. At one extreme, complementary portions 302 and 303 of the housing and the plug make contact, and thereby seal the opening 301 completely. As the plug is withdrawn upwardly, the variable shapes 304 and 305 at the end of the plug 210 alter the flow characteristics in a predetermined manner. Finally, when the plug is withdrawn completely from the opening 301, such as shown in FIG. 3, substantially no occlusion is provided to the flow through opening 301. It is to be understood that the shapes and inclinations of surfaces 303, 304, and 305 are variable in accordance with the needs of the designer.

Referring back to FIG. 2, it may be seen that the plug 210 is provided with a protuberance 209' which serves as a limiting stop to the upward adjustment of the plug 210. The threaded engagement of the plug 210 with the upper portion 208 of the valve housing provides a fine vernier control over the amount of occlusion presented by the plug 210 to the outlet port 201 of the cavity 202.

The accuracy of this control is further promoted by provision of a knob 212 attached to the upper end of the plug 210, which includes a cylindrical flange extending downwardly and coaxially over the upper portion 208 of the valve housing. A recess in the housing 208 carries an O-ring 211, which in turn provides a retentive force to the knob 212, and in turn allows for extremely stable positioning of the plug 210.

As set forth hereinbefore, the lower threaded portion 222 of the valve engages corresponding female apparatus in the patient circle. In order to insure that the valve will be there positioned with the exhaust nozzle 214 pointing in the appropriate direction, a lock nut 218 is provided which may be tightened downwardly against the female receptacle, thereby holding the valve in an established position with the exhaust nozzle 214 pointing as desired. Recesses 220 are provided in the lock nut 218 to facilitate tightening thereof, and an O-ring 219 engages the housing 201 and the lock nut 218 in order to insure a firm and vibration free interconnection of the two.

The functioning of the ball 205 in the cavity 202 is similar to that set forth in connection with post-operative respiratory exercise devices such as those set forth in U.S. Application Ser. No. 401,130 of John R. Boehringer, filed Sept. 27, 1973 and assigned to the assignee hereof. That application sets forth configurations of the cavity and alternative compositions of the ball. An additional consideration in accordance with the principles of the present invention, however, relates to the fact that the valve is performing a critical function in a vacuum exhausted anesthesia system. Thus, not only must the size of the ball 205 and the opening 217 on which it seats be carefully calibrated, but such calibration must account also for venturi effects and pressure differentials to which the ball is subjected. Given the configuration shown and a particular specific gravity and volume of the ball, and diameter of the orifice 217 may be evaluated analytically. Empirically, this diameter is imprecise, and the orifice must be machined slightly to yield the proper function. This is true even if the ball is ground and polished, and the orifice 217 is machined at the analytical diameter to extremely high degrees of precision. On the other hand, the degree to which the diameter must be altered is not susceptible to guantilative evaluation, but instead must be individually calibrated for each valve using essentially empirical methods. Once determined, the configuration may be reproduced using precision molding techniques.

In a preferred analytical design, the cavity forming insert 203 has an upper surface 223 inclined at approximately a 10° angle to the vertical, and a lower ledge inclined at 39° to vertical. The ball 205 is composed nylon, has a diameter of 0.625 inches, and is ground and polished, and the diameter of the orifice 217 is 0.406 inches. Such design parameters analytically indicates the clinically desirable ball back pressure of 2.5 centimeters $H_2O$. In fact, however, the true diameter of the orifice at 217 must be made incrementally larger, which enlarging is accomplished by means of precision machining in an empirical testing process (i.e., measure, machine, measure again, and so on).

The foregoing is submitted as a preferred illustration of the principles of the present invention, but it is to be understood that numerous alternative embodiments will occur to those of ordinary skill without departing from the spirit or scope thereof.

I claim:

1. In a vacuum exhausted anesthesia administration system, valve apparatus for regulating gas pressure in the patient anesthesia circle comprising:
   generally vertically disposed housing means having an inlet port at a lower end engaging said circle and an outlet port at an upper end feeding the vacuum exhaust, said housing means defining at least one cavity therein, communicating respectively with said inlet ports, said cavity having an opening of predetermined diameter at said inlet port and a generally frustoconical shape from said opening upwardly increasing in diameter toward said outlet port;
   means for coupling said inlet port to said patient circle;
   means for coupling said outlet port to said vacuum exhaust;
   a ball freely movable movable within said cavity, said ball having a diameter larger than said predetermined diameter, said ball having predetermined specific gravity to provide continuous predetermined back pressure to gases at said inlet port; and
   adjustably movable piston means having an end portion matable with said outlet port for sealable closure, said end portion of said piston means having at least two successive, differently inclined surfaces, one of said surfaces sealably mating with said outlet port and the other of said surfaces being configured to produce predetermined variable occlusion of said outlet port in response to adjustment of said piston means.

2. Apparatus as described in claim 1 wherein said piston means is in threaded engagement with said housing means and wherein the mating end of said piston means terminates in a characterized, varying diameter plug for blocking said outlet port variably in accordance with adjustment of said piston means, adjustment of said piston means towards or away from said outlet port effectively presenting an occlusion of correspondingly adjusted diameter by changing the portion of said plug which is occluding said outlet port.

3. In a system for providing anesthesia, apparatus for regulating the flow of gas through the system, which comprises:
   a. housing means forming a generally frustonconical chamber having an opening at the bottom through which gas can enter, the inner diameter of the chamber being smallest at said opening and increasing at respective first and second slopes in the upward direction;
   b. a partition dividing the chamber into upper and lower sections, and having an orifice at its center;
   c. a ball freely movable within the lower section of the chamber, said ball having a diameter smaller than the extreme diameter of said first slope, but larger than said opening, whereby said ball is sufficiently large to cover completely the opening at the bottom of the chamber;
   d. a screw which screws into the upper section of the chamber and extends to said orifice; and
   e. a plug at the bottom of the screw, which variably blocks the orifice in accordance with operation of the screw relative to the partition.

4. Apparatus as recited in claim 3, which further comprises input means for mounting said apparatus to an anesthesia circle, including:
   a. a hollow cylinder threaded on its outer surface concentric with the opening at the bottom of the chamber, connected to and protruding downwardly from said housing means;
   b. a flexible ring attached around the threaded cylinder;
   and
   c. a spanner lock nut which screws onto the threaded cylinder, in engagement with said ring, whereby said apparatus is mounted to anesthesia circle apparatus by said threaded cylinder, and locked thereon by operation of said spanner nut.

5. Apparatus as recited in claim 3, which further comprises:
   a. an O-ring engaged around the upper section of the chamber;
   b. a knob connected to said screw including a flange having a diameter larger than that of the upper section of the chamber, and which engages said O-ring when the screw is screwed into the upper section of the chamber.

6. In a vacuum exhausted anesthesia administration system, valve apparatus for regulating gas pressure in the patient anesthesia circle comprising:
   generally vertically disposed housing means having an inlet port at a lower end engaging said circle and an outlet port at an upper end feeding the vacuum exhaust, said housing means defining at least one cavity therein, communicating respectively with said inlet and outlet ports, said cavity having an opening of predetermined diameter at said inlet port and a generally frustoconical shape from said opening upwardly increasing in diameter toward said outlet port;
   means for coupling said inlet port to said patient circle;
   means for coupling said outlet port to said vacuum exhaust;
   a ball freely movable within said cavity, said ball having a diameter larger than said predetermined diameter, said ball having predetermined specific gravity to provide continuous predetermined back pressure to gases at said inlet port; and
   adjustably movable piston means having an end portion matable with said outlet port for sealable closure, said end portion of said piston means having at least two successive, differently inclined surfaces, one of said surfaces sealably mating with said outlet port and the other of said surfaces being configured to produce predetermined variable occlusion of said outlet port in response to adjustment of said piston means, and further including a transverse bar across said outlet port within said cavity to prevent occlusion of said outlet port by said ball.

* * * * *

UNITED STATES PATENT OFFICE
CERTIFICATE OF CORRECTION

Patent No. 4,026,284  Dated May 31, 1977

Inventor(s) John R. Boehringer

It is certified that error appears in the above-identified patent and that said Letters Patent are hereby corrected as shown below:

Column 3, line 14 before "nozzle" insert --exhaust--

Column 4, line 46, "guantilative" should be --quantilative--

Column 5, line 9, after "inlet" insert --and outlet--

Signed and Sealed this sixteenth Day of August 1977

[SEAL]

Attest:

RUTH C. MASON
Attesting Officer

C. MARSHALL DANN
Commissioner of Patents and Trademarks